(12) United States Patent
Hirata et al.

(10) Patent No.: US 8,242,285 B2
(45) Date of Patent: Aug. 14, 2012

(54) N-TERT-BUTOXYCARBONYL-2-PYRROLIDI-NONES AND PRODUCTION METHOD THEREOF

(75) Inventors: Norihiko Hirata, Suita (JP); Toshitsugi Uemura, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 9 days.

(21) Appl. No.: 12/838,661

(22) Filed: Jul. 19, 2010

(65) Prior Publication Data
US 2010/0280259 A1 Nov. 4, 2010

Related U.S. Application Data

(62) Division of application No. 12/297,111, filed as application No. PCT/JP2006/313356 on Jun. 28, 2006, now abandoned.

(30) Foreign Application Priority Data

Apr. 17, 2006 (JP) ................................. 2006-113072

(51) Int. Cl.
C07D 209/52 (2006.01)
(52) U.S. Cl. ........................................................ 548/512
(58) Field of Classification Search .................. None
See application file for complete search history.

(56) References Cited

U.S. PATENT DOCUMENTS

| | | | |
|---|---|---|---|
| 5,024,994 | A | 6/1991 | Doherty et al. |
| 5,397,846 | A | 3/1995 | Eichhorn et al. |
| 6,423,845 | B1 | 7/2002 | Rivera et al. |
| 2004/0147764 | A1 | 7/2004 | Kraatz |

FOREIGN PATENT DOCUMENTS

| | | |
|---|---|---|
| JP | 5-221879 A | 8/1993 |
| JP | 05247047 A | 9/1993 |
| JP | 6-092918 A | 4/1994 |
| JP | 2001-151744 A | 6/2001 |
| JP | 2002-338544 A | 11/2002 |
| JP | 2003-514908 A | 4/2003 |
| JP | 2004-238322 A | 8/2004 |
| WO | 98/05327 A1 | 2/1998 |
| WO | 01/38328 A1 | 5/2001 |
| WO | 02/081442 A2 | 10/2002 |
| WO | 2004/052850 A2 | 6/2004 |
| WO | WO 2004/092134 | * 10/2004 |

OTHER PUBLICATIONS

Morikawa et al. J. Org. Chem. 1994, 59, 97-103.*
Hermet et al. Synthetic Communications, 36: 2253-2257, 2006.*
Gawley et al., "Structural studies of {6Li} 2-lithiopyrrolidines using NMR spectroscopy", Tetrahedron, vol. 61, No. 13, pp. 3271-3280, (2005).
Hanessian et al., "Synthesis of Diversely Functionalized Indolizidinones and Related Bicyclic Lactams Using Intramolecular Grubbs Olefin Metathesis and Dieckmann Condensation", Journal of Organic Chemistry, vol. 68, No. 19, pp. 7219-7233, (2003).
Campbell et al., "Chirospecific Syntheses of Precursors of Cyclopentane and Cyclopentene Carbocyclic Nucleosides by [3+3]-Coupling and Transannular Alkylation", Journal of Organic Chemistry, vol. 60, No. 14, pp. 4602-4616, (1995).
Tverezovsky et al., "Synthesis of (2S, 3R, 4S)-3,4-Methanoproline and Analogues by Cyclopropylidene Insertion", Tetrahedron, vol. 53, No. 43, pp. 14773-14792, (1997).
Morikawa et al., "Synthesis of Optically Active cis- and trans-1,2-Disubstituted Cyclopropane Derivatives by the Simmons-Smith Reaction of Allyl Alcohol Derivatives Derived from (R)-2,3-O-Isopropylideneglyceraldehyde", Journal of Organic Chemistry, vol. 59, No. 1, pp. 97-103, (1994).
Shuto et al., "Synthesis of Conformationally Restricted Analogs of Baclofen, a Potent GABAB Receptor Agonist, by the Introduction of a Cyclopropane Ring", Chem. Pharm. Bull., vol. 47, No. 8, pp. 1188-1192, (1999).
Matsuki et al., "Enantioselective Reduction of meso-Cyclic-1,2-dicarboxylic Anhydrides and 1,2-Dicarboximides: Asymmetric Synthesis of bycyclic Lactones and hydroxylactams", Che, Pharm. Bull. 42(1), 9-18, (1994).

(Continued)

Primary Examiner — Joseph K. McKane
Assistant Examiner — Alicia L Otton
(74) Attorney, Agent, or Firm — Panitch Schwarze Belisario & Nadel LLP

(57) ABSTRACT

N-tert-butoxycarbonyl-2-pyrrolidinones represented by the following formula (1).

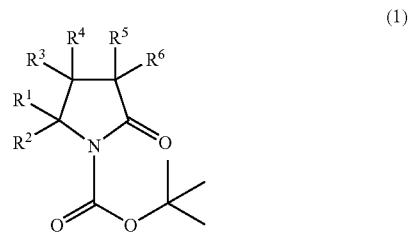

(1)

In the formula (1), R1, R2, R3, R4, R5 and R6 independently represent a hydrogen atom, a halogen atom, a cyano group, a linear, branched or cyclic alkyl group having 1 to 10 carbon atoms, which may have a substituent, a linear, branched or cyclic alkenyl group having 2 to 10 carbon atoms, which may have a substituent, or the like, R1 and R2 may be linked to form a >C=O group along with the carbon atom to which both are attached, R3 and R4 may be linked to form a >C=O group along with the carbon atom to which both are attached, R5 and R6 may be linked to form a >C=O group along with the carbon atom to which both are attached, or any two among R1, R2, R3, R4, R5 and R6 may be linked to form a polymethylene group having 1 to 4 carbon atoms which may have a substituent.

2 Claims, No Drawings

OTHER PUBLICATIONS

"dichloromethane (Methylene Chloride)", Substance profiles, From National Toxicology Program, Department of Health and Human Services. <http://ntp.niehs.nih.gov/ntp/roc/eleventh/profiles/s066 dich.pdf>, Jan. 2005.

Bonnaud et al., Stereoselective Synthesis of cis and trans 2-Substituted 1-Phenyl-3-azabicyclo[3.1.0]hexanes., J. Heterocyclic Chem., 30 (2), pp. 505-508, (1993).

* cited by examiner

N-TERT-BUTOXYCARBONYL-2-PYRROLIDINONES AND PRODUCTION METHOD THEREOF

CROSS-REFERENCE TO RELATED APPLICATIONS

This application is a divisional of co-pending U.S. application Ser. No. 12/297,111, filed Oct. 14, 2008, the disclosure of which is incorporated herein by reference.

BACKGROUND OF THE INVENTION

The present invention relates to N-tert-butoxycarbonyl-2-pyrrolidinones, and a production method thereof.

Conventionally, for N-tert-butoxycarbonylation (hereinafter, abbreviated simply as N-Boc formation in some cases) using di-tert-butyl dicarbonate of 2-pyrrolidinones, there are known a method of using acetonitrile as a reaction solvent (see, Tetrahedron, 61(13), 3271 (2005)), a method of using N,N-dimethylformamide as a reaction solvent (see, WO-2002081442), a method of using tetrahydrofuran as a reaction solvent (see, U.S. Pat. No. 5,024,994), a method of using triethylamine as a reaction solvent (see, WO-9805327), a method of using a non-polar halogen-based solvent (see, J. Org. Chem., 68(19), 7219 (2003)) and the like.

These methods using polar solvents have a problem that if water-washing is performed for the purpose of removing a base used together in the reaction, separation of a polar solvent and water is difficult, thus, washing with water should be carried out after once substitution with a hydrophobic organic solvent. In the case of use of a halogen solvent such as methylene chloride and the like (see, J. Org. Chem., 68(19), 7219 (2003)), there is a problem of toxicity of the vapor of the solvent. That is, all the methods are not necessarily satisfactory as an industrial production method.

The present inventors have investigated a method for N-Boc formation of 2-pyrrolidinones, showing little of the problems as described above, and resultantly found a method of N-Boc formation of 2-pyrrolidinones in an aromatic solvent. Further, the present inventors have found novel N-tert-butoxycarbonyl-2-pyrrolidinones.

BRIEF SUMMARY OF THE INVENTION

The present invention has an object of providing a method of producing N-tert-butoxycarbonyl-2-pyrrolidinones, advantageous also from the industrial standpoint That is, the present invention provides the following [1] to [12].

[1]. N-tert-butoxycarbonyl-2-pyrrolidinones of the following formula (1):

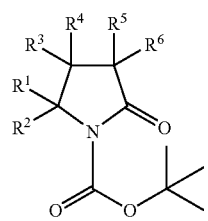

(1)

wherein, $R^1$, $R^2$, $R^3$, $R^4$, $R^5$ and $R^6$ represent each independently a hydrogen atom, halogen atom, cyano group, optionally substituted linear, branched or cyclic alkyl group having 1 to 10 carbon atoms, optionally substituted linear, branched or cyclic alkenyl group having 2 to 10 carbon atoms, optionally substituted aryl group having 6 to 20 carbon atoms, optionally substituted amino group, $-OR_a$ group, or $-SR_b$ group, $R_a$ and $R_b$ represent each independently a hydrogen atom, alkylcarbonyl group having 2 to 10 carbon atoms, arylcarbonyl group having 7 to 20 carbon atoms, aralkyl group having 7 to 20 carbon atoms, alkoxyalkyl group having 2 to 10 carbon atoms, trialkylsilyl group having 3 to 10 carbon atoms, alkyl group having 1 to 10 carbon atoms, aryl group having 6 to 20 carbon atoms, alternatively, $R^1$ and $R^2$ may be connected to form a >C=O group together with a carbon atom to which they are connected, $R^3$ and $R^4$ may be connected to form a >C=O group together with a carbon atom to which they are connected, $R^5$ and $R^6$ may be connected to form a >C=O group together with a carbon atom to which they are connected, any two of $R^1$, $R^2$, $R^3$, $R^4$, $R^5$ and $R^6$ may be connected to form an optionally substituted polymethylene group having 1 to 4 carbon atoms, one or no-mutually-adjacent two methylene groups constituting the polymethylene group may be substituted by an oxygen atom, one or two ethylene groups constituting the polymethylene group may be substituted by a vinylene group, no-mutually-adjacent two methylene groups constituting the polymethylene group may be mutually connected via an oxygen atom, methylene group, ethylene group or vinylene group.

[2]. The N-tert-butoxycarbonyl-2-pyrrolidinones according to [1], wherein $R^1$, $R^2$, $R^3$, $R^4$, $R^5$ and $R^6$ in the formula (1) represent each independently a hydrogen atom or an optionally substituted linear or branched alkyl group having 1 to 3 carbon atoms, alternatively, any two of $R^1$, $R^2$, $R^3$, $R^4$, $R^5$ and $R^6$ are connected to form an optionally substituted polymethylene group having 1 to 4 carbon atoms.

[3]. The N-tert-butoxycarbonyl-2-pyrrolidinones according to [1], wherein $R^1$, $R^2$, $R^4$ and $R^6$ in the formula (1) represent a hydrogen atom, and $R^3$ and $R^5$ are connected to form an optionally substituted polymethylene group having 1 to 4 carbon atoms.

[4]. 3-tert-butoxycarbonyl-6,6-dimethyl-3-azabicyclo[3.1.0]hexan-2-one.

[5]. (1R,5S)-3-tert-butoxycarbonyl-6,6-dimethyl-3-azabicyclo[3.1.0]hexan-2-one.

[6]. A method of producing N-tert-butoxycarbonyl-2-pyrrolidinones, comprising reacting 2-pyrrolidinones of the following formula (2):

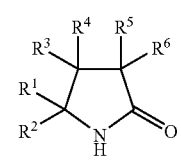

(2)

wherein, $R^1$, $R^2$, $R^3$, $R^4$, $R^5$ and $R^6$ represent the same meanings as described above, with di-tert-butyl dicarbonate in an aromatic solvent, thereby producing N-tert-butoxycarbonyl-2-pyrrolidinones of the following formula (1):
wherein, $R^1$, $R^2$, $R^3$, $R^4$, $R^5$ and $R^6$ represent the same meanings as described above.

[7]. The production method according to [6], wherein the reaction is carried out in the presence of a base in an aromatic solvent.

[8]. The production method according to [6] or [7], wherein the aromatic solvent is an aromatic hydrocarbon solvent.

[9]. The production method according to [8], wherein the aromatic hydrocarbon solvent is toluene.

[10]. The production method according to any one of [6] to [9], wherein $R^1$, $R^2$, $R^3$, $R^4$, $R^5$ and $R^6$ in the formulae (1) and (2) represent each independently a hydrogen atom or an optionally substituted linear or branched alkyl group having 1 to 3 carbon atoms, alternatively, any two of $R^1$, $R^2$, $R^3$, $R^4$, $R^5$ and $R^6$ are connected to form an optionally substituted polymethylene group having 1 to 4 carbon atoms.

[11]. The production method according to any one of [6] to [9], wherein $R^1$, $R^2$, $R^4$ and $R^6$ in the formulae (1) and (2) represent a hydrogen atom, and $R^3$ and $R^5$ are connected to form an optionally substituted polymethylene group having 1 to 4 carbon atoms.

[12]. The production method according to any one of [6] to [9], wherein $R^1$, $R^2$, $R^4$ and $R^6$ in the formulae (1) and (2) represent a hydrogen atom, and $R^3$ and $R^5$ are connected to form a $(CH_3)_2C<$ group.

DETAILED DESCRIPTION OF THE INVENTION

Modes for Carrying Out the Invention

The present invention will be illustrated in detail below.

N-tert-butoxycarbonyl-2-pyrrolidinones of the formula (1) [hereinafter, abbreviated as Boc-2-pyrrolidinones (1) in some cases] can be obtained by reacting 2-pyrrolidinones of the formula (2) [hereinafter, abbreviated as 2-pyrrolidinones (2) in some cases] with di-tert-butyl dicarbonate in an aromatic solvent. This reaction is preferably carried out in the presence of a base in an aromatic solvent.

$R^1$, $R^2$, $R^3$, $R^4$, $R^5$ and $R^6$ in the above-described 2-pyrrolidinones (2) represent each independently a hydrogen atom, halogen atom, cyano group, optionally substituted linear, branched or cyclic alkyl group having 1 to 10 carbon atoms, optionally substituted linear, branched or cyclic alkenyl group having 2 to 10 carbon atoms, optionally substituted aryl group having 6 to 20 carbon atoms, optionally substituted amino group, —$OR_a$ group, or —$SR_b$ group, $R_a$ and $R_b$ represent each independently a hydrogen atom, alkylcarbonyl group having 2 to 10 carbon atoms, arylcarbonyl group having 7 to 20 carbon atoms, aralkyl group having 7 to 20 carbon atoms, alkoxyalkyl group having 2 to 10 carbon atoms, trialkylsilyl group having 3 to 10 carbon atoms, alkyl group having 1 to 10 carbon atoms, aryl group having 6 to 20 carbon atoms.

Alternatively, $R^1$ and $R^2$ may be connected to form a >C=O group together with a carbon atom to which they are connected, $R^3$ and $R^4$ may be connected to form a >C=O group together with a carbon atom to which they are connected, $R^5$ and $R^6$ may be connected to form a >C=O group together with a carbon atom to which they are connected.

Alternatively, any two of $R^1$, $R^2$, $R^3$, $R^4$, $R^5$ and $R^6$ may be connected to form an optionally substituted polymethylene group having 1 to 4 carbon atoms. One or no-mutually-adjacent two methylene groups constituting the polymethylene group may be substituted by an oxygen atom or sulfur atom, one or two ethylene groups constituting the polymethylene group may be substituted by a vinylene group. No-mutually-adjacent two methylene groups constituting the polymethylene group may be mutually connected via an oxygen atom, sulfur atom, methylene group, ethylene group or vinylene group. As the substituent optionally substituted on the polymethylene group having 1 to 4 carbon atoms, the same substituents as those represented by $R^1$, $R^2$, $R^3$, $R^4$, $R^5$ and $R^6$ described above are mentioned.

It is preferable that $R^1$, $R^2$, $R^3$, $R^4$, $R^5$ and $R^6$ represent each independently a hydrogen atom or an optionally substituted linear or branched alkyl group having 1 to 3 carbon atoms, alternatively, any two of these groups are connected to form an optionally substituted polymethylene group having 1 to 4 carbon atoms.

Further, it is preferable that $R^1$, $R^2$, $R^4$ and $R^6$ represent a hydrogen atom, and $R^3$ and $R^5$ are connected to form an optionally substituted polymethylene group having 1 to 4 carbon atoms.

Here, the halogen atom includes a chlorine atom, bromine atom, fluorine atom, iodine atom.

Examples of the optionally substituted alkyl group having 1 to 10 carbon atoms include linear alkyl groups having 1 to 10 carbon atoms such as a methyl group, ethyl group, n-propyl group, isopropyl group, n-butyl group and the like; cyclic alkyl groups having 3 to 10 carbon atoms such as a cyclopentyl group, cyclohexyl group and the like; halogenated alkyl groups such as a chloromethyl group, dichloromethyl group, trichloromethyl group, fluoromethyl group, difluoromethyl group, trifluoromethyl group and the like; hydroxyalkyl groups such as a hydroxymethyl group or hydroxyethyl group and the like optionally substituted with a substituent such as an acetyl group, benzoyl group, benzyl group, phenyl group, methyl group, methoxymethyl group, trimethylsilyl group and the like; aminoalkyl groups such as an aminomethyl group, aminoethyl group and the like optionally having a substituent such as an acetyl group, benzoyl group, methyl group, benzyl group, phenyl group, tert-butoxycarbonyl-group, benzyloxycarbonyl group and the like; hydroxycarbonylalkyl groups such as a hydroxycarbonylmethyl group, hydroxycarbonylethyl group and the like optionally having a substituent such as a methyl group, ethyl group, n-propyl group, isopropyl group, benzyl group and the like; aralkyl groups such as a phenylmethyl group, phenylethyl group and the like optionally substituted with a halogen atom, alkoxy group, hydroxyl group, nitro group, cyano group, alkyl group having 1 to 6 carbon atoms, aryl group and the like.

Examples of the optionally substituted alkenyl group having 2 to 10 carbon atoms include alkenyl groups having 2 to 10 carbon atoms such as a vinyl group, ethenyl group, 1-propenyl group, 2-propenyl group, 1-butenyl group, 2-butenyl group, 3-butenyl group and the like; hydroxycarbonylalkenyl groups such as a hydroxycarbonylethenyl group and the like optionally substituted with a substituent such as a methyl group, ethyl group, n-propyl group, isopropyl group, benzyl group and the like.

Examples of the optionally substituted aryl group having 6 to 20 carbon atoms include a phenyl group, naphthyl group and the like optionally substituted with a halogen atom, alkoxy group, hydroxyl group, nitro group, cyano group, alkyl group having 1 to 6 carbon atoms and the like.

Examples of the optionally substituted amino group include amino groups optionally substituted with a substituent such as an acetyl group, benzoyl group, methyl group, benzyl group, tert-butoxycarbonyl-group, benzyloxycarbonyl group and the like, and oxime groups such as a hydroxyimino group, methoxyimino group and the like.

Examples of $R_a$ of the —$OR_a$ group include a hydrogen atom, alkylcarbonyl groups having 1 to 10 carbon atoms such as an acetyl group and the like, arylcarbonyl groups having 6 to 20 carbon atoms such as a benzoyl group and the like, arylalkyl groups having 6 to 20 carbon atoms such as a benzyl group and the like, alkoxyalkyl groups having 1 to 10 carbon atoms such as a methoxymethyl group and the like, trialkylsilyl groups having 1 to 10 carbon atoms such as a trimethylsilyl group and the like, alkyl groups having 1 to 10 carbon atoms such as a methyl group, ethyl group, n-propyl group, isopropyl group, tert-butyl group and the like, aryl groups having 6 to 20 carbon atoms such as a phenyl group, and the like.

Examples of $R_b$ of the —$SR_b$ group include a hydrogen atom, alkylcarbonyl groups having 1 to 10 carbon atoms such as an acetyl group and the like, arylcarbonyl groups having 6 to 20 carbon atoms such as a benzoyl group and the like, arylalkyl groups having 6 to 20 carbon atoms such as a benzyl group and the like, alkoxyalkyl groups having 1 to 10 carbon atoms such as a methoxymethyl group and the like, trialkylsilyl groups having 1 to 10 carbon atoms such as a trimethylsilyl group and the like, alkyl groups having 1 to 10 carbon atoms such as a methyl group, ethyl group, n-propyl group, isopropyl group, tert-butyl group and the like, aryl groups having 6 to 20 carbon atoms such as a phenyl group, and the like.

As the specific structure of the group to be formed by connecting any two of $R^1$, $R^2$, $R^3$, $R^4$, $R^5$ and $R^6$, divalent groups of the following formulae, and the like are mentioned.
—$CH_2$—, —$(CH_2)_2$—, —$(CH_2)_3$—, —$(CH_2)_4$—, $(CH_3)_2$C<, $(Cl)_2$C<, $(F)_2$C<, >$CH(CO_2C_2H_5)$

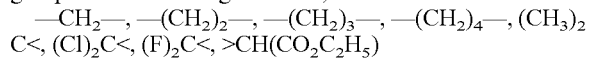

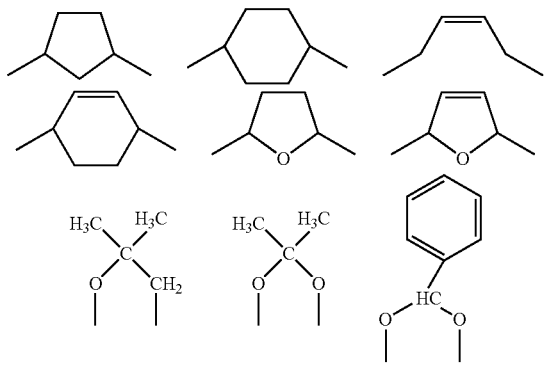

Examples of the 2-pyrrolidinones(2) include 2-pyrrolidinone, 3-methyl-2-pyrrolidinone, 4-methyl-2-pyrrolidinone, 5-methyl-2-pyrrolidinone, 4,4-dimethyl-2-pyrrolidinone, 5,5-dimethyl-2-pyrrolidinone, 3-ethyl-2-pyrrolidinone, 4-propyl-2-pyrrolidinone, 4-cyclohexyl-2-pyrrolidinone, 4-methyl-4-propyl-2-pyrrolidinone, 2-azabicyclo[3,1,0]hexan-3-one, 3-azabicyclo[3.1.0]hexan-2-one, 6,6-dimethyl-3-azabicyclo[3.1.0]hexan-2-one, 2-azabicyclo[2.2.1]heptan-3-one, 2-azabicyclo[3.3.0]octan-3-one, 3-azabicyclo[3.3.0]octan-2-one, 7-azabicyclo[4.3.0]nonan-8-one, 8-azabicyclo[4.3.0]nonan-7-one, 4-azatricyclo[5.2.1.0$^{2.6}$]decan-3-one, 4-azatricyclo[5.2.2.0$^{2.6}$]undecan-3-one, 2-azaspiro[4.4]nonan-3-one, spiro[bicyclo[2.2.2]octan-2,3'-pyrrolidin]-5'-one, 3-(2-propenyl)-2-pyrrolidinone, 2-azabicyclo[2.2.1]hepta-5-en-3-one, 3-azabicyclo[3.2.0]heptan-2-one, 2-azabicyclo[3.3.0]octa-7-en-3-one, 8-azabicyclo[4.3.0]nonan-3-en-7-one, 4-azatricyclo[5.2.1.0$^{2.6}$]decan-8-en-3-one, 4-azatricyclo[5.2.2.0$^{2.6}$]undecan-8-en-3-one, 6,6-dichloro-3-azabicyclo[3.1.0]hexan-2-one, 6,6-difluoro-3-azabicyclo[3.1.0]hexan-2-one, 3-benzyl-2-pyrrolidinone, 5-benzyl-2-pyrrolidinone, 4-benzyl-4-methyl-2-pyrrolidinone, 6-ethoxycarbonyl-3-azabicyclo[3.1.0]hexan-2-one, ethyl 2-(5-oxopyrrolidin-2-yl)acetate, methyl 3-(2-oxopyrrolidin-3-yl)acrylate, 3-phenyl-2-pyrrolidinone, 4-phenyl-2-pyrrolidinone, 5-diphenyl-2-pyrrolidinone, 5-(3-hydroxyphenyl)-2-pyrrolidinone, 1-phenyl-3-azabicyclo[3.1.0]hexan-2-one, 4-chloro-2-pyrrolidinone, 4,4-difluoro-2-pyrrolidinone, 4-hydroxy-2-pyrrolidinone, 3-hydroxy-2-pyrrolidinone, 4-acetoxy-2-pyrrolidinone, 4-methoxy-2-pyrrolidinone, 4-tert-butoxy-2-pyrrolidinone, 4-benzyloxy-2-pyrrolidinone, 4-phenyloxy-2-pyrrolidinone, 3-hydroxy-4-methyl-2-pyrrolidinone, 3-hydroxy-3-methyl-2-pyrrolidinone, 4-hydroxy-5-hydroxymethyl-2-pyrrolidinone, 3,3-dimethyl-2,4-dioxa-7-azabicyclo[3.3.0]octan-6-one, 3-phenyl-2,4-dioxa-7-azabicyclo[3.3.0]octan-6-one, 3,3-dimethyl-2-oxa-7-azabicyclo[3.3.0]octan-6-one, 1,4-dioxa-7-azaspiro[4.4]nonan-8-one, 4-aza-10-oxa-tricyclo[5.2.1.0$^{2.6}$]decan-3-one, 4-aza-10-oxa-tricyclo[5.2.1.0$^{2.6}$]decan-8-en-3-one, 3-hydroxy-9-azabicyclo[4.3.0]nonan-8-one, 4-mercapto-2-pyrrolidinone, 4-mercapto-5-methyl-2-pyrrolidinone, 4-phenylthio-2-pyrrolidinone, 1,4-dithia-7-azaspiro[4.4]nonan-8-one, 1,4-dithia-7-azaspiro[4.4]nonan-6-one, 6,10-dithia-2-azaspiro[4.5]decan-3-one, 4-acetylamino-2-pyrrolidinone, 4-dimethylamino-2-pyrrolidinone, 4-benzylamino-2-pyrrolidinone, 4-benzoylamino-2-pyrrolidinone, 4-tert-butoxycarbonylamino-2-pyrrolidinone, 4-benzyloxycarbonylamino-2-pyrrolidinone, 3-acetylamino-2-pyrrolidinone, 3-dimethylamino-2-pyrrolidinone, 3-benzylamino-2-pyrrolidinone, 3-benzoylamino-2-pyrrolidinone, 3-tert-butoxycarbonylamino-2-pyrrolidinone, 3-benzyloxycarbonylamino-2-pyrrolidinone, 4-tert-butoxycarbonylaminomethyl-2-pyrrolidinone, 5-tert-butoxycarbonylaminomethyl-2-pyrrolidinone, 4-methoxyimino-2-pyrrolidinone, succinic imide, 2,4-pyrrolidinedione and the like, and optically active bodies thereof and the like.

The 2-pyrrolidinones (2) may be produced according to known methods or may be produced by other methods, or commercially available products may be used.

Examples of the base to be used in the reaction include pyridine, quinoline, isoquinoline, N,N-dimethylaminopyridine, 2-picoline, 3-picoline, 4-picoline, 2,3-lutidine, 2,4-lutidine, 2,5-lutidine, 2,6-lutidine, 3,4-lutidine, 3,5-lutidine, 3-chloropyridine, 2-ethyl-3-methylpyridine, 5-ethyl-2-methylpyridine, N,N-dimethylaniline, N,N-diethylaniline, triethylamine, tri-n-butylamine, benzyldimethylamine, N-methylmorpholine, phenethyldimethylamine, N-methylpiperidine, 1,8-diazabicyclo[5.4.0]undec-7-en, 1,4-diazabicyclo[2.2.2]octane, and the like.

These bases can be used singly or in combination of two or more. As the base, it is preferable that N,N-dimethylaminopyridine and triethylamine are used each singly, or these are used in combination. The use amount of the base to be used is usually 0.01 to 5 mole ratio, preferably 0.02 to 1 mole ratio with respect to the 2-pyrrolidinones (2).

Examples of the aromatic solvent to be used in the reaction include benzene, toluene, ethylbenzene, isobutylbenzene, xylene, diethylbenzene, cumene, cymene, diisopropylbenzene, mesitylene, 1,2,4,5-tetramethylbenzene, chlorobenzene, dichlorobenzene, trichlorobenzene, bromobenzene, dibromobenzene, bromochlorobenzene, fluorobenzene, α,α,α-trifluorotoluene, nitrobenzene, nitrochlorobenzene, benzonitrile, styrene, anisole, dimethoxybenzene, ethyl benzoate, di(2-ethylhexyl)phthalate, N,N-dimethylaniline, and the like.

As preferable aromatic solvents, toluene, xylene, chlorobenzene and α,α,α-trifluorotoluene are mentioned. As a particularly preferably solvent, toluene is mentioned.

These solvents may be used in admixture of two or more. The use amount of the aromatic solvent is usually 1 to 50 weight ratio, preferably 1 to 10 weight ratio with respect to the 2-pyrrolidinones (2).

The use amount of di-tert-butyl dicarbonate is usually 1 to 10 mole ratio, preferably 1 to 2 mole ratio with respect to the 2-pyrrolidinones (2).

The above-described reaction is carried out, for example, by mixing 2-pyrrolidinones (2) and di-tert-butyl dicarbonate and an aromatic solvent, if necessary, a base, and adjusting the mixture at desired reaction temperature.

The above-described reaction may also be carried out by dropping a solution composed of di-tert-butyl dicarbonate or di-tert-butyl dicarbonate and a solvent into a solution composed of 2-pyrrolidinones(2) and an aromatic solvent, and if necessary, a base.

The above-described reaction temperature is usually in the range of 0° C. to temperature not higher than the boiling point of the reaction solvent, preferably in the range of 10 to 100° C.

Thus, a reaction solution containing N-Boc-formed 2-pyrrolidinones (1) is obtained. It is possible that, after completion of the reaction, a solvent is distilled off an isolation performed by silica gel column chromatography, however, usually, a post-treatment operation is carried out for removing a base and the like used in the reaction.

In the post-treatment operation, water or an acidic aqueous solution is added to a solution obtained after completion of the N-Boc formation reaction and these are mixed, and liquid partitioning is carried out, thereby removing the above-described base into an aqueous solution. The washing operation with water or an acidic aqueous solution may be carried out repeatedly. It is also permissible that after washing with an acidic aqueous solution, washing is repeated using an alkaline aqueous solution or water.

Examples of the acid to be used in the above-described acidic aqueous solution include inorganic acids (hydrogen chloride, hydrogen bromide, sulfuric acid, phosphoric acid and the like) and organic acids (acetic acid, citric acid and the like). The use amount of these acids is usually in the range of 0.5 to 20 mole ratio, preferably 1 to 5 mole ratio with respect to a base. Examples of the base to be used in carrying out the washing operation with an alkaline aqueous solution include alkali metal hydroxides (sodium hydroxide, potassium hydroxide and the like), alkali metal carbonates (sodium carbonate, potassium carbonate and the like), alkali metal bicarbonates (sodium hydrogen carbonate, potassium hydrogen carbonate and the like), etc.

In the post-treatment, the aromatic solvent used in the reaction is usually used as it is, and for the purpose of dissolving the product or improving liquid partitioning property, an organic solvent other than the aromatic solvents may be added in performing the washing operation. The kind and use amount of the organic solvent other than the aromatic solvents are not particularly restricted.

Thus obtained solution can be subjected to concentration of an organic solvent and the like, to isolate Boc-2-pyrrolidinones (1). The Boc-2-pyrrolidinones (1) may be further purified by column chromatography, re-crystallization and the like.

The method of re-crystallization is not particularly restricted, and usual re-crystallization methods may be used.

Examples of the re-crystallization method include a method in which a crystal is deposited by dropping a poor solvent after dissolving in a good solvent, a method in which Boc-2-pyrrolidinones (1) are dissolved in a re-crystallization solvent with heating, then, the solution is cooled to deposit a crystal, a method in which after dissolving in a re-crystallization solvent, the solvent is distilled off by concentration, to cause deposition of a crystal, combinations of these methods, and the like.

When the Boc-2-pyrrolidinones (1) are optically active bodies, if the above-described re-crystallization is carried out, the optical purity of the optically active body is improved in some cases.

$R^1$, $R^2$, $R^3$, $R^4$, $R^5$ and $R^6$ in the Boc-2-pyrrolidinones (1) represent the same meanings as for $R^1$, $R^2$, $R^3$, $R^4$, $R^5$ and $R^6$ defined in the 2-pyrrolidinones (2).

Specific examples of the Boc-2-pyrrolidinones (1) include N-tert-butoxycarbonyl-2-pyrrolidinone, N-tert-butoxycarbonyl-3-methyl-2-pyrrolidinone, N-tert-butoxycarbonyl-4-methyl-2-pyrrolidinone, N-tert-butoxycarbonyl-5-methyl-2-pyrrolidinone, N-tert-butoxycarbonyl-4,4-dimethyl-2-pyrrolidinone, N-tert-butoxycarbonyl-5,5-dimethyl-2-pyrrolidinone, N-tert-butoxycarbonyl-3-ethyl-2-pyrrolidinone, N-tert-butoxycarbonyl-4-propyl-2-pyrrolidinone, N-tert-butoxycarbonyl-4-cyclohexyl-2-pyrrolidinone, N-tert-butoxycarbonyl-4-methyl-4-propyl-2-pyrrolidinone, 2-tert-butoxycarbonyl-2-azabicyclo[3,1,0]hexan-3-one, 3-tert-butoxycarbonyl-3-azabicyclo[3.1.0]hexan-2-one, 6,6-dimethyl-3-tert-butoxycarbonyl-3-azabicyclo[3.1.0]hexan-2-one, 2-tert-butoxycarbonyl-2-azabicyclo[2.2.1]heptan-3-one, 2-tert-butoxycarbonyl-2-azabicyclo[3.3.0]octan-3-one, 3-tert-butoxycarbonyl-3-azabicyclo[3.3.0]octan-2-one, 7-tert-butoxycarbonyl-7-azabicyclo[4.3.0]nonan-8-one, 8-tert-butoxycarbonyl-8-azabicyclo[4.3.0]nonan-7-one, 4-tert-butoxycarbonyl-4-azatricyclo[5.2.1.0$^{2.6}$]decan-3-one, 4-tert-butoxycarbonyl-4-azatricyclo[5.2.2.0$^{2.6}$]undecan-3-one, 2-tert-butoxycarbonyl-2-azaspiro[4.4]nonan-3-one, N-tert-butoxycarbonyl-spiro[bicyclo[2.2.2]octan-2,3'-pyrrolidin]-5'-one, N-tert-butoxycarbonyl-3-(2-propenyl)-2-pyrrolidinone, 2-tert-butoxycarbonyl-2-azabicyclo[2.2.1]hepta-5-en-3-one, 3-tert-butoxycarbonyl-3-azabicyclo[3.2.0]heptan-2-one, 2-tert-butoxycarbonyl-2-azabicyclo[3.3.0]octa-7-en-3-one, 8-tert-butoxycarbonyl-8-azabicyclo[4.3.0]nonan-3-en-7-one, 4-tert-butoxycarbonyl-4-azatricyclo[5.2.1.0$^{2.6}$]decan-8-en-3-one, 4-tert-butoxycarbonyl-4-azatricyclo[5.2.2.0$^{2.6}$]undecan-8-en-3-one, 6,6-dichloro3-tert-butoxycarbonyl-3-azabicyclo[3.1.0]hexan-2-one, 6,6-difluoro-3-tert-butoxycarbonyl-3-azabicyclo[3.1.0]hexan-2-one, N-tert-butoxycarbonyl-3-benzyl-2-pyrrolidinone, N-tert-butoxycarbonyl-5-benzyl-2-pyrrolidinone, N-tert-butoxycarbonyl-4-benzyl-4-methyl-2-pyrrolidinone, N-tert-butoxycarbonyl-6-ethoxycarbonyl-3-azabicyclo[3.1.0]hexan-2-one, ethyl N-tert-butoxycarbonyl-2-(5-oxopyrrolidin-2-yl)acetate, methyl N-tert-butoxycarbonyl-3-(2-oxopyrrolidin-3-yl)acrylate, N-tert-butoxycarbonyl-3-phenyl-2-pyrrolidinone, N-tert-butoxycarbonyl-4-phenyl-2-pyrrolidinone, N-tert-butoxycarbonyl-5-diphenyl-2-pyrrolidinone, N-tert-butoxycarbonyl-5-(3-hydroxyphenyl)-2-pyrrolidinone, 1-phenyl-3-tert-butoxycarbonyl-3-azabicyclo[3.1.0]hexan-2-one, N-tert-butoxycarbonyl-4-chloro-2-pyrrolidinone, N-tert-butoxycarbonyl-4,4-difluoro-2-pyrrolidinone, N-tert-butoxycarbonyl-4-hydroxy-2-pyrrolidinone, N-tert-butoxycarbonyl-3-hydroxy-2-pyrrolidinone, N-tert-butoxycarbonyl-4-acetoxy-2-pyrrolidinone, N-tert-butoxycarbonyl-4-methoxy-2-pyrrolidinone, 2,4-di-tert-butoxy-2- pyrrolidinone, N-tert-butoxycarbonyl-4-benzyloxy-2-pyrrolidinone, N-tert-butoxycarbonyl-4-phenyloxy-2-pyrrolidinone, N-tert-butoxycarbonyl-3-hydroxy-4-methyl-2-pyrrolidinone, N-tert-butoxycarbonyl-3-hydroxy-3-methyl-2-pyrrolidinone, N-tert-butoxycarbonyl-4-hydroxy-5-hydroxymethyl-2-pyrrolidinone, 3,3-dimethyl-2,4-dioxa-7-tert-butoxycarbonyl-7-azabicyclo[3.3.0]octan-6-one, 3-phenyl-2,4-dioxa-7-tert-butoxycarbonyl-7-azabicyclo[3.3.0]octan-6-one, 3,3-dimethyl-2-oxa-7-tert-butoxycarbonyl-7-azabicyclo[3.3.0]octan-6-one, 1,4-dioxa-7-tert-butoxycarbonyl-7-azaspiro[4.4]nonan-8-one, 4-tert-butoxycarbonyl-4-aza-10-oxa-tricyclo[5.2.1.0$^{2.6}$]decan-3-one, 4-tert-butoxycarbonyl-4-aza-10-oxa-tricyclo[5.2.1.0$^{2.6}$]decan-8-en-3-one, 3-hydroxy-9-tert-butoxycarbonyl-9-azabicyclo[4.3.0]nonan-8-one, N-tert-butoxycarbonyl-4-mercapto-2-pyrrolidinone, N-tert-butoxycarbonyl-4-mercapto-5-methyl-2-pyrrolidinone, N-tert-butoxycarbonyl-4-phenylthio-2-pyrrolidinone, 1,4-dithia-7-tert-butoxycarbonyl-7-azaspiro[4.4]nonan-8-one, 1,4-dithia-7-tert-butoxycarbonyl-7-azaspiro[4.4]nonan-6-one, 6,10-dithia-2-tert-butoxycarbonyl-2-azaspiro[4.5]decan-3-one, 1-tert-butoxycarbonyl-4-acetylamino-2-pyrrolidinone, 1-tert-butoxycarbonyl-4-dimethylamino-2-pyrrolidinone, 1-tert-butoxycarbonyl-4-benzylamino-2-pyrrolidinone, 1-tert-butoxycarbonyl-4-benzoylamino-2-pyrrolidinone, 1-tert-butoxycarbonyl-4-tert-butoxycarbonylamino-2-pyrrolidinone, 1-tert-butoxycarbonyl-4-benzyloxycarbonylamino-2-pyrrolidinone, 1-tert-butoxycarbonyl-3-acetylamino-2-pyrrolidinone, 1-tert-butoxycarbonyl-3-dimethylamino-2-pyrrolidinone, 1-tert-butoxycarbonyl-3-benzylamino-2-pyrrolidinone, 1-tert-butoxycarbonyl-3-benzoylamino-2-pyrrolidinone, 1-tert-butoxycarbonyl-3-tert-butoxycarbonylamino-2-pyrrolidinone, 1-tert-butoxycarbonyl-3-benzyloxycarbonylamino-2-pyrrolidinone, 1-tert-butoxycarbonyl-4-tert-butoxycarbonylaminomethyl-2-pyrrolidinone, 1-tert-butoxycarbonyl-5-tert-butoxycarbonylaminomethyl-2-pyrrolidinone, 1-tert-butoxycarbonyl-4-methoxyimino-2-pyrrolidinone, N-tert-butoxycarbonyl-succinic imide, N-tert-butoxycarbonyl-2,4-pyrrolidinedione and the like, and optically active bodies thereof, and the like.

According to the present invention, N-tert-butoxycarbonyl-2-pyrrolidinones which are useful as a chemical raw material or medical-agricultural drug intermediate can be provided.

According to the present invention, 3-tert-butoxycarbonyl-6,6-dimethyl-3-azabicyclo[3.1.0]hexan-2-one which is useful as a chemical raw material or medical-agricultural drug intermediate can be provided.

Further, according to the present invention, (1R,5S)-3-N-tert-butoxycarbonyl-6,6-dimethyl-3-azabicyclo[3.1.0]hexan-2-one which is useful as a chemical raw material or medical-agricultural chemical precursor can be provided.

According to the N-Boc formation reaction of the present invention, it is not necessary to substitute a water-soluble polar solvent by a hydrophobic solvent in the post-treatment operation and it is not necessary to use a solvent of strong harmful effect, thus, special harm-protecting equipments and the like are not required, and N-tert-butoxycarbonyl-2-pyrrolidinones can be produced simply and industrially advantageously.

The N-tert-butoxycarbonyl-2-pyrrolidinones of the present invention are useful as a chemical raw material or medical-agricultural drug intermediate, and for example, can be suitably used as a production intermediate of the following compound (see, WO2004/113295) which is one of anti-hepatitis C drugs (HCV drugs).

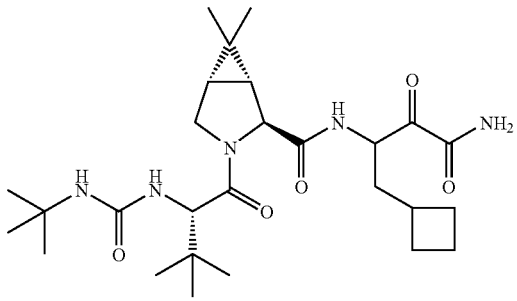

EXAMPLES

The present invention will be illustrated in further detail based on examples below, but it is needless to say that the present invention is not limited to these examples.

Example 1

Production Example of 3-tert-butoxycarbonyl-6,6-dimethyl-3-azabicyclo[3.1.0]hexan-2-one To 1158.5 g of a toluene solution containing 195.5 g (1.562 mol) of 6,6-dimethyl-3-azabicyclo[3.1.0]hexan-2-one was added 19.08 g (0.156 mol) of N,N-dimethylaminopyridine and these were dissolved at 25° C. Into this solution, a solution composed of 443.2 g (2.031 mol) of di-tert-butyl dicarbonate and 195.5 g of toluene was dropped over a period of 2 hours, and the mixture was thermally insulated at 25° C. for 12 hours.

To this solution was added 569.5 g of 1% hydrochloric acid and mixed, and liquid-partitioning was caused. An organic layer obtained by liquid-partitioning was washed with 262.5 g of a 5% sodium hydrogen carbonate aqueous solution, further washed with 262.5 g of water, then, 1652.8 g of a toluene solution containing 349.7 g (1.552 mol) of 3-tert-butoxycarbonyl-6,6-dimethyl-3-azabicyclo[3.1.0]hexan-2-one was obtained. The yield with respect to 6,6-dimethyl-3-azabicyclo[3.1.0]hexan-2-one was 99.4%.

The determinate quantity of 3-tert-butoxycarbonyl-6,6-dimethyl-3-azabicyclo[3.1.0]hexan-2-one was obtained by high performance liquid chromatography. As the column, SUMIPAX ODS D-210FF, 4.6 mmϕ×150 mm, 3 μm (manufactured by Sumika Chemical Analysis Service, Ltd.) was used.

Example 2

Production Example of (1R,5S)-3-tert-butoxycarbonyl-6,6-dimethyl-3-azabicyclo[3.1.0]hexan-2-one To 36.0 kg of a toluene solution containing 5.89 kg (47.1 mol) of (1R,5S)-6,6-dimethyl-3-azabicyclo[3.1.0]hexan-2-one having an optical purity of 93.0% ee was added 0.58 kg (4.75 mol) of N,N-dimethyl-aminopyridine, and these were dissolved at 25° C. Into this solution, a solution composed of 13.36 kg (61.2 mol) of di-tert-butyl dicarbonate and 5.9 kg of toluene was dropped over a period of 3 hours, and the mixture was thermally insulated at 25° C. for 2 hours. The reaction progressed quantitatively.

To this solution was added 17.38 kg of 1% hydrochloric acid and mixed, and liquid-partitioning was caused. Subsequently, the resultant organic layer was washed with 7.89 kg of a 5% sodium hydrogen carbonate aqueous solution, further washed with 7.9 kg of water, to obtain a toluene solution containing (1R,5S)-3-tert-butoxycarbonyl-6,6-dimethyl-3-azabicyclo[3.1.0]hexan-2-one. Most of toluene in this solution was distilled off by concentration under reduced pressure. To this was added 58.8 kg of heptane, and concentration under reduced pressure was carried out to distill off most of the solvent. An operation of substituting this solvent was repeated again, then, to the resultant residue was added 38.7 kg of heptane and the mixture was heated up to 50 to 55° C., to dissolve all the deposited crystal. This solution was cooled down to 45° C., then, a seed crystal of (1R,5S)-3-tert-butoxycarbonyl-6,6-dimethyl-3-azabicyclo[3.1.0]hexan-2-one was added.

After confirmation of deposition of a crystal, it was cooled down to 0° C. The resultant crystal was filtrated, then, washing with 15.9 kg of heptane was carried out twice. Then, the product was dried under reduced pressure.

8.35 kg (37.1 mol) of a crystal of (1R,5S)-3-tert-butoxycarbonyl-6,6-dimethyl-3-azabicyclo[3.1.0]hexan-2-one having an optical purity of 99.6% ee was obtained.

The optical purity was measured by high performance liquid chromatography. As the column, CHIRALCEL OF, 4.6 mm$\phi$×250 mm, 10 μm (manufactured by Daicel Chemical Industries, Ltd.) was used.

The yield of (1R,5S)-3-tert-butoxycarbonyl-6,6-dimethyl-3-azabicyclo[3.1.0]hexan-2-one with respect to (1R,5S)-6,6-dimethyl-3-azabicyclo[3.1.0]hexan-2-one was 78.8%.

The melting point of (1R,5S)-3-tert-butoxycarbonyl-6,6-dimethyl-3-azabicyclo[3.1.0]hexan-2-one was 87 to 88° C.

The results of $^1$H-NMR (CDCl$_3$) are shown below.

δ=3.81 dd (1H), 3.59 d (1H), 1.88 dd (1H), 1.67 dt (1H), 1.56 s (9H), 1.13 s (3H), 1.09 s (3H)

Example 3

Production Example of N-tert-butoxycarbonyl-2-pyrrolidinone 2.55 g (30.0 mmol) of 2-pyrrolidinone, 25.5 g of toluene and 0.37 g (3.0 mmol) of N,N-dimethyl-aminopyridine were added, and the temperature of the mixture was adjusted to 25° C. Into the resultant solution, a solution composed of 8.50 g (39.0 mmol) of di-tert-butyl dicarbonate and 2.55 g of toluene was dropped over a period of 30 minutes, and the mixture was thermally insulated at 25° C. for 8 hours. To the resultant solution was added 10.9 g of 1% hydrochloric acid and mixed, then, liquid-partitioning was caused. The resultant organic layer was washed with 5.0 g of a 5% sodium hydrogen carbonate aqueous solution, then, further washed with 5.0 g of water. The resultant organic layer was concentrated under reduced pressure, to obtain 5.70 g of an oily substance containing 5.30 g (28.6 mmol) of N-tert-butoxycarbonyl-2-pyrrolidinone.

The yield of N-tert-butoxycarbonyl-2-pyrrolidinone with respect to 2-pyrrolidinone was 95.3%.

The determinate quantity of N-tert-butoxycarbonyl-2-pyrrolidinone was obtained by gas chromatography. As the column, DB-5 (0.53 mm$\phi$×30 m, 1.5 μm) manufactured by J&J was used.

Example 4

Production Example of N-tert-butoxycarbonyl-succinic imide 2.97 g (30.0 mmol) of succinic imide, 29.7 g of toluene and 0.37 g (3.0 mmol) of N,N-dimethylaminopyridine were added, and the temperature of the mixture was adjusted to 25° C. Into this solution, a solution composed of 8.79 g (40.3 mmol) of di-tert-butyl dicarbonate and 4.83 g of toluene was dropped over a period of 30 minutes, and the mixture was thermally insulated at 25° C. for 24 hours. To this solution was added 10.9 g of 1% hydrochloric acid and mixed, then, liquid-partitioning was caused. Next, the resultant organic layer was washed with 5.0 g of a 5% sodium hydrogen carbonate aqueous solution, and further washed with 5.0 g of water.

The resultant organic layer was concentrated under reduced pressure, to obtain 5.21 g of an oily substance containing 4.22 g (21.2 mmol) of N-tert-butoxycarbonyl-succinic imide.

The yield of N-tert-butoxycarbonyl-succinic imide with respect to succinic imide was 70.7%.

The determinate quantity of N-tert-butoxycarbonyl-succinic imide was obtained by gas chromatography. As the column, DB-1 [0.25 mm$\phi$×30 m, 0.25 μm] manufactured by J&J was used.

Industrial Applicability

N-tert-butoxycarbonyl-2-pyrrolidinones obtained by the production method of the present invention are useful as chemical raw materials or medical-agricultural drug intermediates.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:
1. 3-tert-butoxycarbonyl-6,6-dimethyl-3-azabicyclo [3.1.0]hexan-2-one.
2. (1R,5S)-3-tert-butoxycarbonyl-6,6-dimethyl-3-azabicyclo[3.1.0]hexan-2-one.

* * * * *